(12) United States Patent
Erspamer et al.

(10) Patent No.: US 6,559,081 B1
(45) Date of Patent: May 6, 2003

(54) MULTIFUNCTIONAL FIBROUS MATERIAL WITH IMPROVED EDGE SEAL

(75) Inventors: John P. Erspamer, Bartlett, TN (US); Jeffrey S. Hurley, Bartlett, TN (US); Brian E. Boehmer, Bartlett, TN (US); Derrix Betts, Memphis, TN (US)

(73) Assignee: BKI Holding Corporation, Wilmington, DE (US)

( * ) Notice: Subject to any disclaimer, the term of this patent is extended or adjusted under 35 U.S.C. 154(b) by 0 days.

(21) Appl. No.: 09/578,603

(22) Filed: May 25, 2000

Related U.S. Application Data (60) Provisional application No. 60/135,912, filed on May 25, 1999, and provisional application No. 60/166,489, filed on Nov. 19, 1999.

(51) Int. Cl.[7] .............................. B32B 27/02; B32B 5/26
(52) U.S. Cl. ...................... 442/392; 442/385; 442/393; 442/411; 442/415; 442/416; 442/417; 428/165; 428/166; 428/167; 428/168; 428/196; 604/367
(58) Field of Search .................................. 442/381, 389, 442/385, 393, 409, 411, 415, 416, 417, 392; 428/166, 167, 168, 320.2, 165, 195, 196; 604/367

(56) References Cited

U.S. PATENT DOCUMENTS

| 5,843,267 | A | * | 12/1998 | Cashaw et al. | ............. | 156/324 |
| 5,938,650 | A | * | 8/1999 | Baer et al. | .................. | 604/368 |
| 6,162,959 | A | | 12/2000 | O'Connor | .................... | 602/41 |

* cited by examiner

Primary Examiner—Terrel Morris
Assistant Examiner—Jenna-Leigh Befumo
(74) Attorney, Agent, or Firm—Darby & Darby (57) ABSTRACT

This invention relates to fibrous absorbent articles containing particles useful in the manufacture of disposable diapers, adult incontinence pads, sanitary napkins and the like, scrubbing pads, scouring pads and cleaning pads that contain a detergent or soap and the like, and pads that contain coffee, tea, and the like More particularly, the invention is directed to an absorbent articles having sealed lateral edges to contain loose fibers and particles within the structure. Additionally, this invention is related to airlaid methods to manufacture unitary absorbent products.

28 Claims, 3 Drawing Sheets

MULTIFUNCTIONAL FIBROUS MATERIAL WITH IMPROVED EDGE SEAL

This application claims priority under 35 U.S.C. § 119, based on U.S. provisional patent application serial No. 60/135,912, filed May 25, 1999, and U.S. provisional patent application serial No. 60/166,489, filed Nov. 19, 1999, the entire disclosures of which are hereby incorporated by reference.

FIELD OF THE INVENTION

This invention relates to multifunctional fibrous structures containing particles, which are useful in the manufacture of disposable diapers, adult incontinence pads, sanitary napkins and the like, scrubbing pads, scouring pads and cleaning pads that contain a detergent or soap and the like, and pads that contain coffee, tea, and the like. More particularly, the invention is directed to fibrous articles having sealed lateral edges to contain fibers and particles within the structure.

BACKGROUND OF THE INVENTION

Fibrous structures may be used as absorbent articles, cleaning pads containing a detergent, coffee or tea bags.

Absorbent articles such as disposable diapers, adult incontinence pads, sanitary napkins, panty liners and the like, are generally provided with an absorbent core to receive and retain bodily liquids. The absorbent core is usually sandwiched between a liquid pervious top sheet, whose function is to allow the passage of fluid to the core, and a liquid impervious backsheet, whose function is to contain the fluid and to prevent it from passing through the absorbent article to the garment of the wearer of the absorbent article.

An absorbent core for diapers and adult incontinence pads frequently includes fibrous batts or webs constructed of defiberized, loose, fluffed, hydrophilic, cellulosic fibers. The core may also include a layer or stratum containing superabsorbent polymer (SAP) particles, granules, flakes or fibers, often referred to as the storage layer or stratum.

In recent years, market demand for an increasingly thinner and more comfortable absorbent article has increased. Such an article may be obtained by decreasing the thickness of the diaper core, by reducing the amount of fibrous material used in the core while increasing the amount of SAP particles, and by calendering or pressing the core to reduce caliper and hence, increase density.

Such higher density cores do not absorb liquid as rapidly as lower density cores because the compacting of the core (densification) results in smaller effective pore size. Accordingly, to maintain suitable liquid absorption, it is necessary to provide a lower density layer having a larger pore size above the highdensity absorbent core to increase the rate of uptake of liquid discharged onto the absorbent article. The low-density layer is typically referred to as an acquisition layer. Multiple layer absorbent core designs involve a more complicated manufacturing process.

The storage layer portion of a disposable diaper for example, is generally formed in place, during the converting process, from loose, fluffed cellulose. Such cellulose material is generally not available in preformed roll form because it exhibits insufficient web strength, owing to its lack of interfiber bonding or entanglement, to be unwound directly onto and handled in absorbent pad-making equipment.

Ultra-thin feminine napkins are generally produced from roll-goods based nonwoven material. Such a roll of preformed absorbent core material is unwound directly onto the absorbent article converting equipment without the defiberization step required for fluff-based products, such as diapers and incontinence pads. The nonwoven web is typically bonded or consolidated in a fashion that gives it sufficient strength to be handled in the converting process. These webs may also contain SAP particles.

The web consolidation mechanisms used in the roll-goods approach to making preformed cores provide strength and dimensional stability to the web. Such mechanisms include latex bonding, bonding with thermoplastic or bicomponent fibers or, thermoplastic powders, hydroentanglement, needlepunching, carding or the like. At high particle loading, however, the core structures exhibit poor particle containment. In other words, some of the particles tend to escape from the structure during manufacture, handling, shipping and converting and in use. This can result in the fouling of manufacturing and converting equipment as well as negative consumer perception of the product.

There is a need for an absorbent core material which facilitates fluid transport from an acquisition zone to a storage zone, exhibits good particle containment at high particle loading, is thin but has a high absorbent capacity in use, and can be delivered in roll-goods form to simplify the manufacturing and converting processes.

It is an object of the invention to provide a fibrous web comprising functional particles, which can be formed into absorbent articles containing functional particles having improved properties of particle containment and reduced amounts of delamination and powder spillage.

It is an object of the invention to provide a method of forming an edge seal in a fibrous article, to provide improved containment of functional particles which are present in the absorbent article.

It is another object of the invention to provide an improved method of disposing functional particles in a fibrous absorbent article, to provide an effective absorbent article having improved properties of strength and particle containment, and reduced amounts of particle spillage.

SUMMARY OF THE INVENTION

It has now been surprisingly and unexpectedly discovered that a fibrous article containing functional particles can be made with an air laid process using certain binders to facilitate strong edge seals, without the loss of functional particles through powder spillage.

In a first embodiment, the invention is directed to a fibrous web which comprises a lower stratum comprising matrix fibers and a thermoplastic bonding material; and an upper stratum comprising matrix fibers and a thermoplastic bonding material. The web further comprises a plurality of functional particle areas which are positioned between the upper and lower strata so as to contact each of the upper and lower strata. The functional particle areas are separated from other functional particle areas by a particle-free seal area comprising a seal formed between the upper and lower strata.

The seal area may be formed by compacting (densification) the upper and lower strata, for example by the application of pressure or heat. Alternatively, and or additionally, a binder may be applied to the seal area. Upon curing, the binder will serve to aid in the sealing of the upper and lower strata at the seal area.

In preferred embodiments, the seal area is substantially free of functional particles. in another embodiment, the invention is directed to a fibrous structure containing lower and upper strata comprising matrix fibers and optionally a thermoplastic bonding material; a functional particle area positioned between the upper and lower strata so as to contact each of the upper and lower strata; and a seal area comprising a seal formed between the upper and lower strata, wherein the seal area is substantially free of functional particles. In preferred embodiments, the fibrous article has at least two seal areas, wherein the seal areas are disposed on opposing edges of the article. The fibrous structure may be disposed as an absorbent core in a product, such as a disposable diaper, adult incontinence pad, sanitary napkin and the like. Alternatively, the fibrous structure can be used as a pad that contains coffee, tea, and the like, or a scrubbing pad, scouring pad and cleaning pad that contains a detergent or soap and the like.

In preferred embodiments, the upper and lower strata comprise cellulosic or synthetic fibers and a thermoplastic bonding material, such as bicomponent fibers; and the particle area includes particles such as super absorbent polymers (SAP), and odor control agents, such as zeolite or calcium carbonate.

In one embodiment, the invention is directed to an absorbent article (such as a diaper, sanitary napkin, or adult incontinence garment) which contains a fluid pervious topsheet; a fluid impervious backsheet; and an absorbent core disposed therebetween, wherein the absorbent core comprises a first stratum which contains matrix fibers and a thermoplastic bonding material and a second stratum which contains matrix fibers and a thermoplastic bonding material; and wherein one of the first or second strata is in fluid contact with the fluid pervious topsheet or the fluid impervious backsheet. Functional particles are disposed between the second and third strata. In addition, a seal area is formed between the second and third strata, wherein the seal area is substantially free of functional particles.

In still another embodiment, the invention is directed in part to a process for making an airlaid unitary fibrous structure, such as a fibrous web or absorbent core of the type described above. The process includes the steps of:

(a) providing a first stratum of a fibrous web;

(b) positioning functional particles in a first area on the first stratum;

(c) providing a second stratum of a fibrous web;

(d) positioning the second stratum on the first stratum so as to contact the first stratum and the particles;

(e) sealing the first and second strata at the non-particle area, thereby forming a discrete particle area positioned between the upper and lower strata; and (f) curing the structure at a temperature of from 125 to 180° C.

The process of the invention may also include the use of a binder. In a first application, a binder may be applied to the web so as to contact an area of the web which is free of particles, in order to strengthen the seal area. Additionally, the process of the invention may also include the steps of applying a second binder to the upper and lower strata to minimize dust off and to immobilize the particles contained in the structure; and (h) curing the structure at a temperature of from 125 to 1 80° C.

In particular embodiments, the invention is directed to methods of making absorbent structures.

DETAILED DESCRIPTION OF THE INVENTION

All patent and patent applications cited in this specification are hereby incorporated by reference into this specification. In case of conflict in terminology, the present disclosure controls.

The present invention is directed to a unitary, multilayer structure, including a lower stratum or layer containing matrix fibers, such as cellulosic or synthetic fibers, or blends thereof. The structure also includes an upper stratum or layer also containing matrix fibers of cellulosic or synthetic fibers, which is positioned above the lower layer. Either the lower layer or the upper layer preferably also includes a thermoplastic bonding material, in either powder or fiber form. Exemplary fibrous thermoplastic binding materials are bicomponent thermoplastic fibers.

Sandwiched between the upper and lower layers is a functional particle area. The particle area is disposed so that it is in contact with each of the upper and lower strata. The particle area is applied in portions or zones but does not cover the entire lower layer.

In one embodiment, the particles are deposited to form lanes on the lower layer. The zones between the lanes therefore are particle-free zones or lanes, and contain substantially no particles. A second stratum of matrix fibers is deposited onto the lower stratum containing the functional particles.

Seals may be formed by binding the upper stratum to the lower stratum in the particle-free zones or lanes. In certain embodiments, wherein at least one of the upper and lower strata include a thermoplastic binding material, seals are formed when the structure is compacted or densified by pressure or pressure and heat. The seals may be further strengthened by subsequent curing in a curing oven.

In an alternative embodiment, the particle-free areas may be sealed by the application of a liquid binder (or binder in a liquid carrier), after compacting or densification of the particle free areas. In such embodiments, the binder is targeted to contact the particle-free areas, and to avoid the particle areas. The binder wicks into the densified region, and forms seals upon drying and curing. Further, in these embodiments, the upper and lower strata optionally contain a thermoplastic binding material.

In another embodiment, seals are formed by application of a liquid binder (or a binder in a liquid carrier) in the particle free zone only, wherein the binder wicks into the densified region and forms strong seals upon drying and curing, without densification of the particle free zone.

In preferred embodiments, seals are formed by compacting or densification of the particle-free areas, followed by application of a binder which is targeted to contact the particle-free areas, and to avoid the particle areas. The binder wicks into the densified region, and forms seals upon drying and curing. In these preferred embodiments, the upper and lower strata each contain a thermoplastic binding material, which strengthens the seals upon densification and curing.

The heat seals are substantially free of functional particles, and the resultant seal is stronger than a seal having particles at the seal interface. When the structure of the invention is subjected to a liquid insult, there are substantially no particles (such as SAP particles) within the sealed area which can swell and disrupt the integrity of the seal.

The articles of the invention may have a range of total basis weights. Preferred total basis weights are from 50 to 1000 gsm (grams per square meter), more preferably from 150 to 600 gsm, even more preferably from 150 to 300 gsm, and most preferably from 150 to 250 gsm.

In certain embodiments of the invention, the article is an absorbent article.

The fibrous structure having improved particle containment may be delivered in roll-goods form, or in other packaging formats such as festooning, and is particularly useful as an absorbent core for disposable absorbent articles such as diapers, adult incontinence pads and briefs, and feminine sanitary napkins.

The Upper and Lower Strata or Layers

The upper and lower strata of matrix fibers may include cellulosic or synthetic fibers or blends thereof. Most preferred is wood cellulose. Also preferred is cotton linter pulp, chemically modified cellulose such as crosslinked cellulose fibers and highly purified cellulose fibers, such as Buckeye HPF (each available from Buckeye Technologies Inc., Memphis, Tenn.). The fluff fibers may be blended with synthetic fibers, for example polyester such as PET, nylon, polyethylene or polypropylene.

The upper and lower strata may also include thermoplastic binding material, which may be blended with the cellulosic or synthetic fibers. Suitable thermoplastic binding material includes thermoplastic fibers, such bicomponent thermoplastic fibers ("bico"). Preferred thermoplastic binding fibers provide enhanced adhesion for a wide range of materials, including synthetic and natural fibers, particles, and synthetic and natural carrier sheets. An exemplary thermoplastic bico fiber is Celbond Type 255 Bico fiber from Hoechst Celanese.

Other suitable thermoplastic fibers include polypropylenes, polyesters, nylons and other olefins, or modifications thereof. A preferred thermoplastic fiber is FiberVisions type AL-Adhesion-C Bicomponent Fiber, which contains a polypropylene core and an activated copolyolefin sheath.

When the matrix fibers are cellulosic or synthetic fibers (or blends thereof), each of the upper and lower strata may preferably include from about 20 to 500 gsm cellulosic or synthetic fibers or blends thereof, more preferably from 20 to 100 gsm, more preferably from 20 to 80 gsm, more preferably from 30 to 50 gsm, and most preferably about 40 gsm. The thermoplastic bonding material may be present in the upper and lower strata in the amount of 2 to 50% by weight, more preferably 3 to 20%, most preferably about 10%.

The Particle Area

The particulate area (or particle area) is intended to receive particles, flakes, powder, granules, or the like.

The particles may include any functional powder or other particles having a particle diameter of up to 3,000 microns ($\mu$). The particle area may include a particle loading of from 2 to 2,000 gsm, more preferably from 2 to 1,000 gsm, even more preferably from 10 to 600 gsm, and most preferably from 100 to 250 gsm.

The particles may be superabsorbent polymers ("SAP") or other functional material. A superabsorbent polymer is a water soluble compound that has been cross-linked to render it water insoluble but still swellable to at least about 15 times its own weight in physiological saline solution. These superabsorbent materials generally fall into three classes, namely starch graft copolymers, cross-linked carboxymethylcellulose derivatives, and modified hydrophilic polyacrylates. Examples of absorbent polymers include hydrolyzed starch-acrylontrile graft co-polymer, saponified acrylic acid ester-vinyl co-polymer, modified cross-linked polyvinyl alcohol, neutralized cross-linked polyacrylic acid, cross-linked polyacrylate salt, and carboxylated cellulose. The preferred superabsorbent materials, upon absorbing fluids, form hydrogels.

The superabsorbent polymer materials have relatively high gel volume and relatively high gel strength as measured by the shear modulus of the hydrogel. Such preferred materials also contain relatively low levels of polymeric materials which can be extracted by contact with synthetic urine. Superabsorbent polymers are well-known and are commercially available. One example is a starch graft polyacrylate hydrogel marketed under the name IM 1000 (Hoechst-Celanese, Portsmouth, Va.). Other commercially available superabsorbent polymers are marketed under the trademark Sanwet (Sanyo Kasei Kogyo Kabushiki, Japan), Sumika Gel (Sumitomo Kagaku Kabushiki Haishi, Japan), Favor (Stockhausen, Garyville, La.) and the ASAP series (Chemdal, Aberdeen, Miss.). Superabsorbent particulate polymers are also described in detail in U.S. Pat. Nos. 4,102,340 and Re. 32, 649. An example of a suitable SAP is surface cross-linked acrylic acid based powder such as Stockhausen 9350 or SX FAM 70 (Greensboro, N.C.).

Binders

Suitable binders for use in the structures of the invention include binders in liquid form or having a liquid carrier, including latex binders. Useful latex binders include vinyl acetate and acrylic ester copolymers, ethylene vinyl acetate copolymers, styrene butadiene carboxylate copolymers, and polyacrylonitriles, and sold, for example, under the trade names of Airbond, Airflex and Vinac of Air Products, Inc., Hycar and Geon of Goodrich Chemical Co., and Fulatex of H. B. Fuller Company. Alternatively, the binder may be a non-latex binder, such as epichlorohydrin and the like.

The invention contemplates two separate binder applications. In the first application, the binder is applied to the structure so as to contact only the particle free area or lane, which is adjacent the areas or lanes containing the particles disposed between the first and second layers. The binder may be applied in the form of a spray, foam, or mist. In preferred embodiments, the binders are diluted to contain 3 to 25% solids, more preferably 6 to 12% solids, most preferably 10%.

A binder which is diluted to have a relatively high solids content (such as 10%) is ideal for acting in the highly compacted, small pore environment of the particle free area, wherein the seals are formed. The environment results in fast wicking, and the high solids content reduces migration of the binder to the other areas of the web.

The second binder application involves application of a binder, in the form of a foam, spray or mist, to substantially the entire surface of the structure (as an "overall binder"), in order to reduce dust-off on the exterior and interior of the structure. In preferred embodiments, the overall binders are diluted to contain 1 to 20% solids, more preferably 2 to 10% solids, even more preferably 2 to 4% solids, and most preferably about 3.5% solids. While the binder will penetrate to reduce dust-off and to immobilize the functional particles, it will not provide a significant contribution to the structural integrity of the web.

The use of two binder applications allows independent control of the seal area stiffness and the non-seal area stiffness. The stiffness of either region can be controlled by the selection of binder type, solids content and amount of binder applied to the respective regions. This addresses the need to deliver requisite seal strength and maintain sufficient flexibility for the comfort of the user.

The preferred non-seal area stiffness (as measured by the Gurley stiffness test TAPPI Method T543 OM-94 (1994)) is less than 200 mg, more preferred is less than 80 mg, and most preferred is less than 160 mg. In the seal area, the preferred stiffness is less than 150 mg, even more preferred is less than 130 mg, and most preferred is less than 115 mg.

Figure 1:
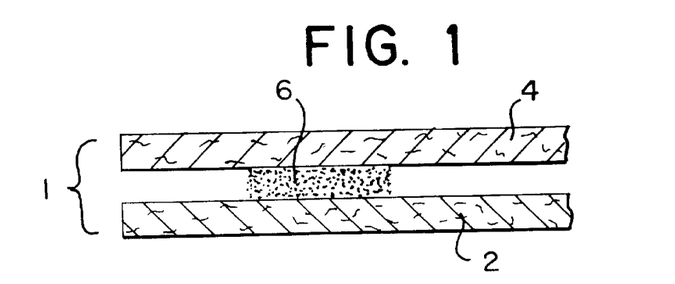
FIG. 1 is a cross-sectional view of a fibrous web or article made according to the present invention showing the upper and lower strata with a particle containing area sandwiched therebetween.

Referring to FIG. 1, there is shown a cross-sectional view of a fibrous web or article 1, including a lower stratum 2, containing matrix fibers (such as cellulosic or synthetic fibers, or blends thereof). The lower stratum 2 preferably also includes a thermoplastic bonding material (in either powder or fiber form, such as a bicomponent thermoplastic fiber). Similarly, an upper stratum 4 is shown, containing fibers of cellulosic or synthetic fibers, or blends thereof The upper stratum preferably also includes a thermoplastic bonding material (in either powder or fiber form such as a bicomponent thermoplastic fiber). This upper and lower strata encloses or sandwiches an area 6 comprising one or more types of functional particles.

Figure 2:
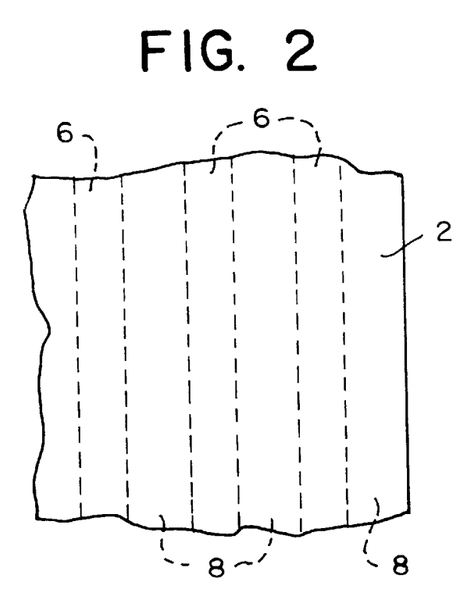
FIG. 2 is a top view of a fibrous web made according to the present invention, showing a web formed with multiple lanes of particle material, forming particle-free zones or gaps.

Now referring to FIG. 2, which is a top view of a fibrous web of the invention, the particle area 6 is present in discontinuous portions or zones that do not cover the entire lower stratum 2. In one embodiment, particles are deposited to form lanes on the lower stratum of the fibrous web.

Figure 3:
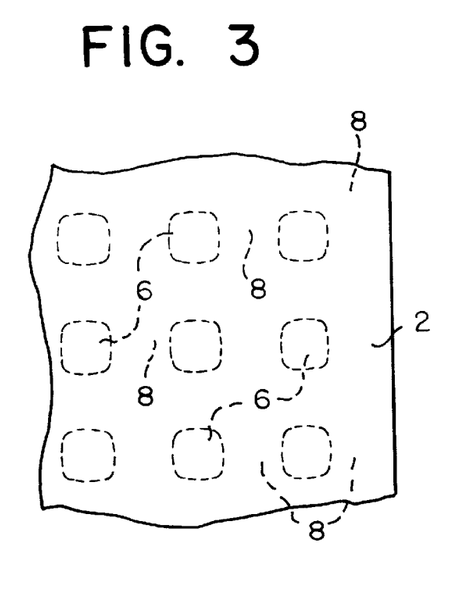
FIG. 3 is a top view of a fibrous web according to the present invention, showing a web formed with multiple lanes of particle material applied intermittently, forming particle-free zones or gaps.

In an alternative embodiment, shown in FIG. 3, which is a top view of a fibrous web of the invention, the particle areas 6 are arranged intermittently, with particle-free areas arranged therebetween. In both FIGS. 2 and 3, the plurality of zones or lanes 8, between the lanes 6, are substantially free of particles.

Figure 4:
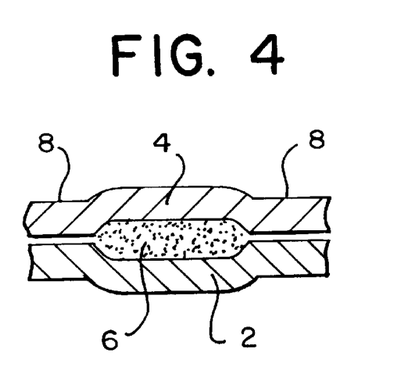
FIG. 4 is a cross-sectional view of an article made according to the present invention showing the upper and lower strata with a particle containing area sandwiched therebetween; after the application of pressure and or heat and pressure.

Now referring to FIG. 4, which is a cross-sectional view of an article made according to the present invention, when the web contains thermoplastic bonding material, the upper and lower strata are bonded together in particle free zones 8 to form a seal which is present between the particle containing areas. The upper and lower strata may be densified by pressure or pressure and heat to form seals between the thermoplastic material and the fibers of the lower stratum 2 and upper stratum 4. Preferred ranges of temperature and pressure for forming the seals is from 0.1 bar at 20° C. to 10 bar at 200° C., more preferably at 90° C. and 2.0 bar. The bond in the seals is further strengthened by curing the thermoplastic material of the fibrous structure in a curing oven or by applying binders onto the seal area. Alternatively, the seals are formed when a liquid binder (or a binder in a liquid carrier) is applied to the densified particle free zone and is wicked into these zones. The binder forms permanent bonds upon thermal curing of the binder material.

Figure 5:
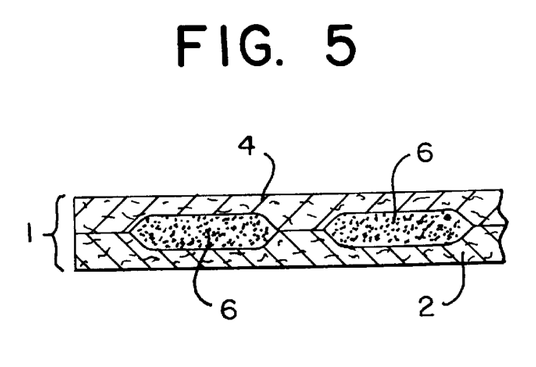
FIG. 5 is a cross-sectional view of an article made according to the present invention showing the upper and lower strata with a particle containing area sandwiched therebetween, after the application of a binder.

Now referring to FIG. 5, a cross-sectional view of an alternative embodiment of the invention is shown wherein a binder is applied to the article 1. The binder bonds the matrix fibers of the upper stratum 4 to the matrix fibers of the lower stratum 2, without the aforementioned compacting or densification process, to yield an article I with a strong edge seal located in an area which is substantially free of particles. Suitable binders, such as aqueous based binder solutions or emulsions, wick in to the seal areas and form a bond upon drying and curing. The amount of binder required is less than 5% of the overall weight of the product. The concentration of binder is determined by the amount necessary to pass through the structure; this amount is generally in the range of from 6 to 12% binder solids.

The resultant seal is stronger than a seal having particles at the seal interface. When the structure of the invention is subjected to a liquid insult, there are substantially no particles within the sealed area, which can swell and disrupt the integrity of the seal. According to the invention, "substantially free" of particles means that any particles present in the seal area are so few as to not interfere with the seal strength.

The fibrous web having improved particle containment may be delivered in roll-goods form or folded in continuous strips, and is particularly useful when formed into an absorbent core for disposable absorbent articles such as diapers, adult incontinence pads and briefs, feminine sanitary napkins and panty liners, and the like. Alternatively, the fibers of the upper and lower strata may be selected to provide scrubbing pads, scouring pads and cleaning pads that contain a detergent or soap, and pads that contain coffee, tea and the like.

Fibrous articles of the invention may have a total or overall density of from 0.05 to 10.0 g/cc, depending on the amount and type of functional particles which are present. Each of the upper and lower strata may have a density of from 0.05 to 0.40 g/cc, and the seal area may have a density of from 0.10 to 0.40 g/cc. When the fibrous article is an absorbent core, preferred density levels are from 0.20 to 0.22 g/cc for the overall density; from 0.150 to 0.250 g/cc for the seal area; and from 0.100 to 0.165 g/cc for each of the upper and lower strata.

During manufacture, the lower stratum may be compacted or densified separately, prior to addition of the particles to the particle area. Subsequently, the particle free areas may be subject to compacting to form seals. The compacting step performed to prepare seals results in a article having increased density in the seal areas, in comparison with the density of the upper and lower strata. If a binder is also applied, the binder will wick in the higher density area. The resulting article will have higher density and lower caliper in the seal area.

The absorbent articles of the invention preferably have a powder spillage value of not more than 1.0 mg. per article and a peak seal strength of greater than 0.6 N. Absorbent articles of the invention have a preferred stiffness of less than 200 mg, preferably less than 180 mg, and most preferably less than 160 mg for the non-seal area; and less than 150 mg, more preferably less than 130 mg, and most preferably less than 115 mg for the seal area.

Airlaid Manufacture of a Structure of the Invention

Preferably, the structure of the present invention is prepared as an airlaid web. The airlaid web is typically prepared by disintegrating or defiberizing a cellulose pulp sheet or sheets, typically by hammermill, to provide individualized fibers. The individualized fibers are then air conveyed to forming heads on the airlaid web forming machine. Several manufacturers make airlaid web forming machines, including M&J Fibretech of Denmark and Dan-Web, also of Denmark. The forming heads include rotating or agitated drums, generally in a race track configuration, which serves to maintain fiber separation until the fibers are pulled by vacuum onto a foraminous condensing drum or foraminous forming conveyor (or forming wire). Other fibers, such as a synthetic thermoplastic fiber, may also be introduced to the forming head through a fiber dosing system which includes a fiber opener, a dosing unit and an air conveyor. Where multiple layers are desired, such as a distribution layer and an acquisition layer, separate forming heads may be provided for each type of layer.

In preferred embodiments, the structures of the invention do not contain a carrier tissue. The use of a compaction roll prior to the introduction of the particle areas eliminates the need for the tissue.

As contemplated by the present invention, one or more forming heads of the airlaid web forming machine distributes the desired fiber for the lower layer of the absorbent structure.

SAP granules or other particles are then applied to the upper surface of this web. Preferably, the particles are applied in lanes in the machine direction with particle-free zones or lanes therebetween. Other particles include odor control agents, e.g., zeolites or calcium carbonate, fragrances, detergents and the like.

A second layer is then formed over the top of the lower layer having the particles applied thereto. Subsequent layers can be formed on top of the second layer.

The airlaid web is transferred from the forming wire to a calender or other densification stage to densify the web, increase its strength and control web thickness. The particle-free zones in the web are subjected to higher pressure or pressure and heat than the other areas. The fibers of the web may alternatively, or additionally, be bonded by application of a binder or foam addition system, followed by drying or curing. As a result, heat seals between the thermoplastic material and the fibers of the upper and lower layers are formed. The heat seals do not include particles (especially SAPs) which could disrupt the heat seal upon exposure to moisture. The finished web is then rolled for future use.

Figure 6:
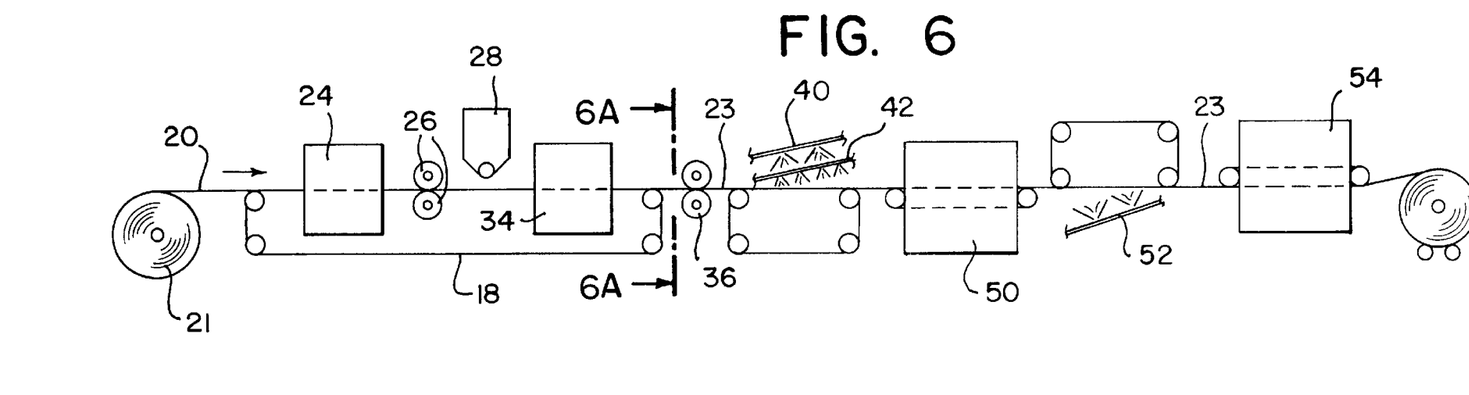
FIGS. 6 and 6A schematically shows a production line for a method of forming absorbent articles comprising an absorbent core according to the present invention.
Figure 6A:
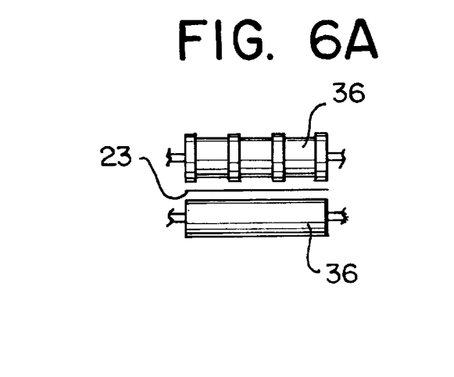

FIG. 6 depicts a process of making a fibrous web according to the present invention. Optionally, a carrier tissue 20 may be unwound from the supply roll 21. The tissue 20 is rolled on to screen 18. The tissue may alternatively be used as a carrier or as the lower stratum 2 of the absorbent article. As contemplated for the present invention, a forming head 24 of the airlaid web-forming machine distributes the desired fiber to form the lower stratum 2 of the absorbent structure. Cellulosic fibers may be obtained by disintegrating or defiberizing a cellulose pulp sheet or sheets, typically by hammermill, to provide individualized fibers. The individualized fibers are then air conveyed to forming heads on the airlaid web-forming machine. Cellulosic fiber and optionally thermoplastic fibers are added to the cellulose tissue 20 by forming head 24.

Several manufacturers make airlaid web forming machines, including M&J Fibretech of Denmark and Dan-Web, also of Denmark. The forming heads include rotating drums, or agitators generally in a racetrack configuration, which serve to maintain fiber separation until the: fibers are pulled by vacuum onto a foraminous condensing drum or foraminous forming conveyor (or forming wire). For example, in machines manufactured by M&J Fibretech, the forming head includes a rotary agitator above a screen. Other fibers, such as a synthetic thermoplastic fiber, may also be introduced to the forming head through a fiber dosing system, which includes a fiber opener, a dosing unit and an air conveyor. Where multiple strata are desired, such as a fluff pulp distribution stratum and a synthetic fiber acquisition stratum, multiple forming heads are provided, one for each type of stratum. In a nip formed by a pair of calender rolls 26, the fibers are optionally compressed to the desired thickness and density. The lower stratum 2 may be compacted at this point in the manufacturing process to close the pores of the web if the particles are fine and to prevent spillage on to the forming wire.

Figure 7:
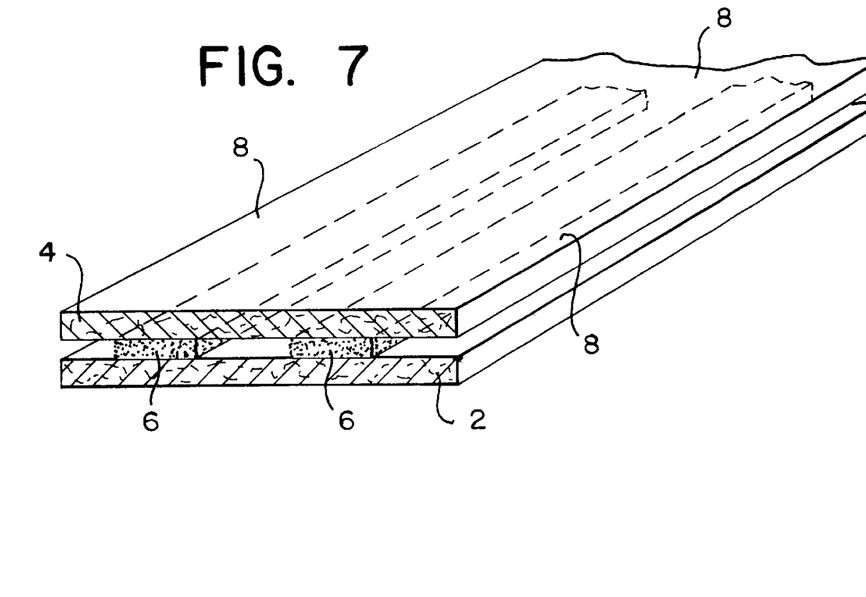
FIG. 7 is a perspective view of a fibrous web on the assembly line.
Figure 8:
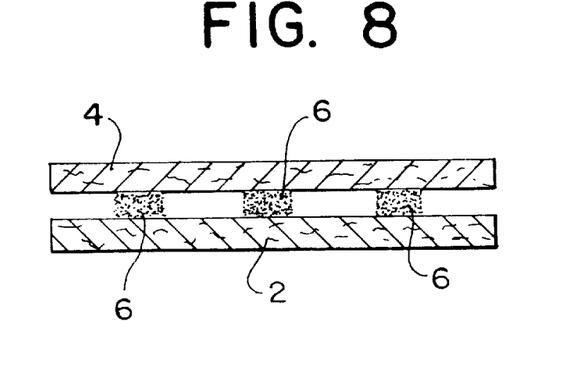
FIG. 8 is a sectional view of the fibrous web of FIG. 7.

Particles are applied to the lower stratum 2 by particle applicator 28. SAP granules or other: particles are thus applied to the upper surface of the lower stratum 2. Referring now to FIG. 7, the particles are applied in a plurality of lanes 6 in the machine direction with particle-free zones or lanes 8 located between the particle lanes. Lanes are areas in which particles are specifically delivered. Other suitable particles include odor control agents, e.g., zeolites or calcium carbonate, fragrances, detergents and the like.

A second strata of fibers 4 is applied by forming head 34, which applies cellulosic fibers, and optionally can also apply a thermoplastic fiber such as a bicomponent fiber. Subsequent layers can be added on top of the second layer.

The airlaid web is transferred from the forming wire 18 to a calender 36 or other densification stage to densify the web, increase its strength and control web thickness. A preferred range of densification is from about 0.050 to about 0.50 g/cc, more preferably about 0.20 g/cc. The particle-free zones in the web are subjected to further treatment including pressure, heat and/or the application of a binder.

The binder is by applied at lane binder applicators 40 and 42, in order to improve or cause heat sealing in the particle free areas. The binder may be applied as a spray, foam or mist. In the preferred embodiment, the web 23 is sprayed with a latex binder, such as AirProducts Airflex 124 or AF192 (cross-linkable latex) or 181 (non-crosslinkable latex), in a concentration of 10% solids. The latex binder spray is concentrated in about a 10 mm width area between the powder lanes 8, so as to concentrate the latex in the edge seal area. The binder may be applied in an amount sufficient to impart about 2 to 15 gsm, preferably about 8 gsm.

In preferred embodiments, the binder may be applied in a range of 4 to 12 mm in width, with a more preferred width of about 10 mm. In preferred embodiments, the overall distance between the lanes is from about 10 to about 12 mm, preferably about 11.5 mm, with the about 10 mm application width centered in the 10 to 12 mmn area.

Surprisingly strong seals with minimal particle inclusion (substantially free of particles), are formed using only the binder applied in the particle free zones or lanes. In this embodiment the fibers of the lower and upper strata fiber need not contain any thermoplastic material, although a thermoplastic material can be included.

A series of ovens is used in processes of the invention, for drying, curing or thermal bonding.

The airlaid web 23 is heated to a temperature in the range of from 125 to 180° C. at oven 50. An overall binder is applied to the airlaid web 23 at 52. This binder can be applied by spray, foam or mist, and is applied to reduce dust-off on the surface of the structure.

The concentration of the binder has sufficient solids to allow the binder to pass through the web. The binder is applied to reduce dust-off on the surface and in the interior of the structure, and to assist the granules in adhering to the interior of the structure. However, the amount of binder applied is insufficient to contribute to the structural integrity of the web. Generally, preformed binder amounts are in the range of 1 to 5%, preferably about 3.5% solids. The total amount of binder applied is preferably less than 5% of the weight of the product. The binder may be applied in an amount sufficient to impart about 2 to 6 gsm, preferably about 4 gsm, to the absorbent structure.

The air laid web 23 is heated in a second oven 54 at a temperature in the range of from 125 to 180° C. The airlaid web 23 can be treated at pressure in the range of from 0.1 to 10 psi, preferably 1.5 psi. As a result of this process, heat seals between the thermoplastic material and the fibers of the upper and lower layers are formed. The heat seals are substantially free of particles (especially SAPs), which could disrupt the heat seal upon exposure to moisture. The finished web is then rolled for future use. This continuous band of fibrous web can be slit or cut to form individual absorbent articles in a cutting unit, which has not been depicted in this figure.

Optionally, the finished web may be slit or perforated at the heat seal to yield narrow slit core material having a heat seal along both edges. The heat seals to be slit must be of sufficient width to provide two effective seals after slitting.

In other embodiments, various other layers containing other types and amounts of fibers may be applied above or below the upper and lower layers of the structure of the present invention. For example, the absorbent article may contain also a fluid previous top sheet and a fluid impervious backsheet. Exemplary absorbent articles which can be formed from absorbent cores of the invention include diapers, feminine sanitary napkins, and adult incontinence products.

Exemplary Embodiments of the Invention

Optionally, a tissue 20 is unwound from the supply roll 21. The tissue 20 is rolled on to screen 18. Weyerhaeuser ND416 pulp is hammermilled to provide individual fibers. The individualized fibers are then air conveyed to forming heads on the airlaid web-forming machine. 44 gsm of Weyerhaeuser ND416 fiber and 4.5 gsm FiberVisions AL-Adhesion-C bicomponent fiber are mixed or applied to the cellulose tissue 20 by forming head 24. The layer is densified. The resulting layer has a denier per filament of 1.5 dpf×4.4 mm.

70 gsm of SAP and 70 gsm of other functional particles are applied to the lower stratum 2 by particle applicators 28 and 30, in a plurality of lanes 6 in the machine direction with particle-free zones 8 therebetween. The particles are striped 27 mm wide with 5.5 mm of unstriped area on both sides. When the lanes are viewed in the machine direction the continuous stripes are 27 mm wide with 11 mm of unstripped area between them.

A second layer of pulp and bico, having the same composition as the first layer, is applied to the web by forming head 34.

The airlaid web is transferred from forming wire 18 to calender 36 to densify the web, increase its strength and control web thickness. Air Products Airflex 124 (10% solids) is sprayed onto the web 23 at the particle free zone. The binder is applied through lane binder applicators .40 and 42. The binder spray is concentrated in about a 11 mm width area between the particle free zones 8, so as to concentrate the latex in the edge seal spray. Strong seals which are substantially free of particles, are formed using only this latex binder. The airlaid web 23 is heated to a temperature in the range of 125 to 180° C. at oven 50.

Air Products Airflex 124 is sprayed to the entire surface of the web 24 at 3.5% solids. The air laid web 23 is heated in a second oven 54 at a temperature in the range of from 125 to 180° C. Optionally, the finished web may be slit or perforated at the heat seal to yield narrow slit core material having a heat seal along both edges. The heat seals to be slit must be of sufficient width to provide two effective seals after slitting. Suitable seals are those having at least 2 mm of width, and preferably 4 mm of width.

Following the general format described above, absorbent cores were prepared. Sample absorbent cores A and B, described below in Table 1, were obtained from the cores produced according to Example 1.

TABLE 1

Absorbent Cores of the Invention

| | Sample Articles | |
|---|---|---|
| | A | B |
| Upper Layer | 40.0 gsm cellulose | 40.0 gsm cellular |
| | 4.5 gsm Bico | 4.5 gsm Bico |
| Particle Area | 70 gsm other functional particles | 70 gsm other functional particles |
| | 70 gsm SAP | 70 gsm SAP |
| Lower Layer | 40.0 gsm cellulose | 40.0 gsm cellulose |
| | 4.5 gsm Biso | 4.5 gsm Bico |
| Lane Binder Spray | 5 gsm | 5 gsm |
| Overall Binder Spray | 4 gsm (top) | 4 gsm (top) |
| | 4 gsm (bottom) | 4 gsm (bottom) |
| Total Basis Weight | 235 gsm | 236 gsm |
| Caliper (mm) | 1.09 | 1.04 |

In sample articles A and B, the cellulose was ND416, the bico was FiberVisions bicomponent fiber, the SAP was Stockhausen FAVOR 1180, the lane binder was Airflex 10 124 (10% solids), and the overall binder was Airflex 124 (3.5% solids).

In preferred embodiments of the absorbent cores of the invention, the particle areas may comprise from 0 to 100% SAP, more preferably from 25 to 75% SAP, and most preferably from 40–70% SAP Table 2 below describes an exemplary preferred embodiment of the absorbent core.

The core may be used in absorbent articles, such as in a feminine hygiene napkin.

TABLE 2

Exemplary Preferred Embodiment

| Head/Location | Raw Material | (gsm) |
|---|---|---|
| Head 1 | ND416 | 40.5 |
| | FiberVisions Bicomponent Fiber (1.55 dpf × 4 mm) | 4.5 |
| | Total Head 1 BW | 44.5 |
| Powder Feed | Other functional particles | 70 |
| | SAP | 70 |
| | Total Powder BW | 139 |
| Head 2 | ND416 | 40.5 |
| | FiberVisions Bicomponent Fiber (1.55 dpf × 4 mm) | 4.5 |
| | Total Head 2 BW | 44.5 |

TABLE 2-continued

Exemplary Preferred Embodiment

| Head/Location | Raw Material | (gsm) |
|---|---|---|
| Lane Binder Spray | Airflex 124 (10% solids) | 5 |
| Overall Binder Spray | | |
| TOP | Airflex 124 (2–4% solids) | 4 |
| BOTTOM | Airflex 124 (2–4% solids) | 4 |
| | Total Binder BW | 12 |
| | TOTAL BW | 242 |

Particle Containment Test

Absorbent articles of the invention may be subjected to a particle containment test. This method is commonly used to evaluate absorbent cores that typically contain superabsorbent polymer (SAP) and/or other particles. Exemplary absorbent cores are those used in feminine hygiene applications.

All samples should be conditioned at 70° F. and 50% relatively humidity prior to testing.

The test measures the ability of a structure to contain particles that have been added to enhance the performance of an absorbent core. The core is shaken at a constant speed for a specified period of time. The particles that are shaken loose are weighed, and this value is reported in units of milligrams. The smaller the weight loss, the better the integrity of the structure.

Product samples may be tested by placing the sample, nonwoven side facing up, on the bottom of a cutting board, and cut about 2 cm into the sample in order to expose the particles. If the product was folded, it should be opened, and a 454 gram weight should be placed on top of it for at least two hours in a conditioned lab.

For laboratory or machine-made airlaid structures, a cutting board should be used, to cut a 200 mm×70 mm (20 cm×7 cm) section. The sample should be evenly cut so that the edges are the same length on the right and left sides of the structure. The sample should then be placed in a conditioned lab for at least 3 hours prior to testing.

For either sample type, the weight, thickness, area and basis weight of the conditioned sample should be determined. The sample should be placed on the corkboard, aligning the top of the sample with the top of the board, fastening the corkboard. Simultaneously switch the power on and start the stopwatch. Shut the unit off after 1 minute, and allow the sample(s) to sit for a few seconds until no particles are falling out of the sample(s).

The particle containment test is conducted as follows. A controlled room is maintained at a temperature and relative humidity of 21.7±0.6° C. (70±2.7° F.) and 50±10% relative humidity. Sufficient air velocity is maintained in the room to diffuse the air near any heat producing areas, and there is be no more than 1.0° C. (1.8° F.) variation in the temperature of the air between any two points in the room. Further, there is no source of water vapor being given off in the room.

The apparatus includes a cutting board; an analytical balance (accuracy/precision:. ±0.0001 g.); a thickness tester with a foot diameter of 41 mm and a load of 150 grams; a timer graduated in 0.1 seconds whose calibration has been verified according to Analytical Method R-7, "Verifying Calibration of Timers"; a particle containment tester with 12" base, 12" sample racks and raised platform; a New Brunswick Scientific "Shaker", Edison,. NJ, Model No.G-33, Mfg No. M1071-0000, Volts 115, Hertz 50/60, Phase 1, Amp 1.0; plexi-glass containers, 6" in height; teflon securing aids and securing bars with knob attachments; and aluminum dishes.

The results of the testing may be calculated as follows:

$$\text{Basis Weight (gsm)} = \frac{\text{Sample Weight (g)} \times 1{,}550 \text{ in}^2/\text{m}^2}{\text{Sample Area (in}^2)}$$

$$\text{Density (g/cc)} = \frac{\text{Sample Weight (g)} \times (1 \text{ in}^3 / 16.39 \text{ cm}^3)}{\text{Sample Area (in}^2) \times \text{Thickness (mm)} \times 0.0394 \text{ in/mm}}$$

$$\text{UncontainedParticles (mg)} =$$
$$[\text{Initial Pan Weight (g)} - \text{Final Pan Weight (g)}] \times \frac{1{,}000 \text{ mg}}{\text{g}}$$

After testing in triplicate, the average uncontained particles (mg) are recorded. Also recorded are sample physical properties, including weight, thickness, area, basic weight and density.

Delamination Test for Feminine Hygiene Structures

The delamination test is used to evaluate multilayered feminine hygiene cores that usually contain superabsorbent polymer (SAP) and/or other particles. The layers are held together by bonding through application of a binder, thermal bonding and/or other forms of bonding. This procedure is used to quantify how well an airlaid structure holds together when subjected to force.

All samples should be conditioned at 70° F. and 50% relative humidity prior to testing.

This method is used to measure the integrity of an airlaid structure as it is subjected to a uniform load at a constant velocity. A force is applied, using a 10 Newton load cell in conjunction with a tensile tester. This procedure will determine the average force and maximum force of resistance associated with the delamination process.

Figure 9:
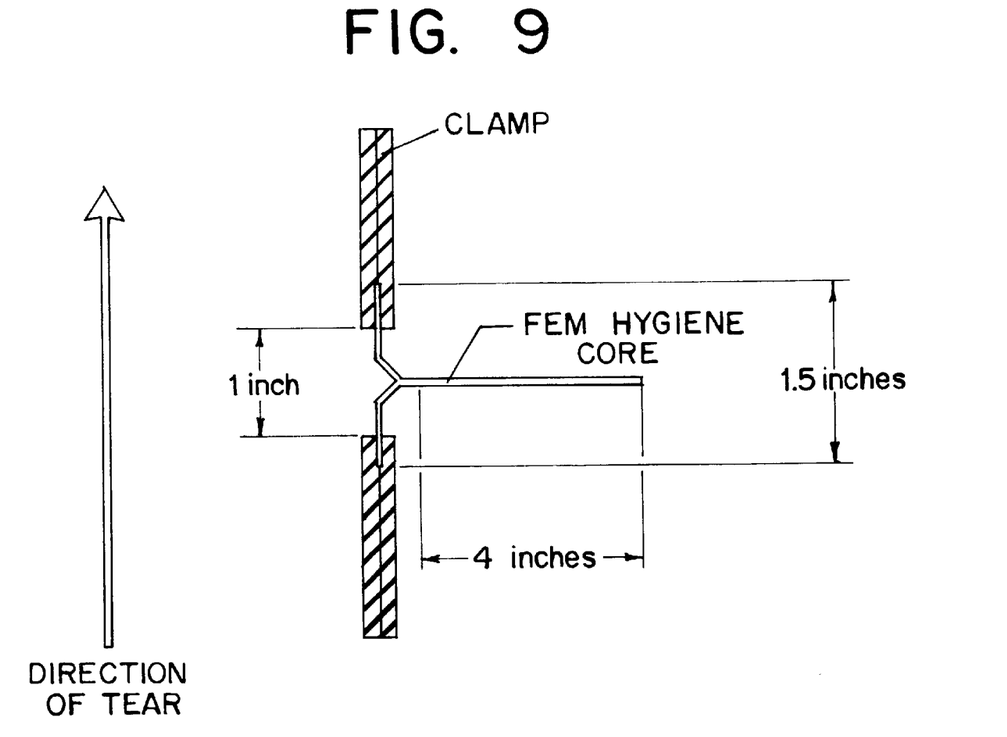
FIG. 9 depicts a schematic of a peel delamination test of a structure of the present invention.

Referring to FIG. 9, using a precision sample cutter, 1 inch samples are cut in the cross direction (CD) (starting from the seal edge and inclusive of the seal area) and 5 inches in the machine direction (MD) (exclusive of the seal area). Approximately 0.75 inches of the laminate on one end in the machine direction (MD) is separated. A 10 Newton load cell is attached to the tensile tester, and the apparatus is set to run a peel/tear test at a clamp distance to 1 inch; a test compression speed to 4 inches/minute; and a length of peel/tear to 4 inches. The initial length start value should be 0.25 inches.

An Instron tensile tester is set to run the peel/tear test. The sample is placed in the grips so that the sample is at the midpoint of both clamps. The maximum and average forces are obtained. The average force, maximum force (Newtons) and standard deviation of both are reported.

This method describes the thickness of absorbent structures that have been conditioned at 73OF and 50% relative humidity, and calculation of density and basis weight of these structures.

The thickness or caliper of an absorbent structure is measured in millimeters using an Edana thickness tester. Typically, a 100 gram load is placed on the tester prior to taking a reading. Using the measured thickness, the density of the structure, in g/cc, also can determined. Also, the basis weight in gsm can be obtained from the collected information.

The sample should be conditioned in the lab for at least three hours prior to testing. Using a cutting board, a section of the pad for testing purposes is cut-out. The sample is weighed, and cleared of lint or debris. A 100 g is placed on the weight stud. A single ply test sample is placed on the anvil of the thickness tester and the presser foot is lowered, making sure not to drop the foot onto the sample. A display reading is recorded.

To calculate the basis weight:

$$\text{Basis Weight (gsm)} = \frac{\text{Sample Weight (g)} \times 1{,}550 \text{ in}^2/\text{m}^2}{\text{Sample Area (in}^2)}$$

To calculate the density:

$$\text{Density (g/cc)} = \frac{\text{Sample Weight (g)} \times (1 \text{ in}^3/16.39 \text{ cm}^3)}{\text{Sample Area (in}^2) \times \text{Thickness (mm)} \times 0.0394 \text{ in/mm}}$$

The average thickness of the sample is recorded, and the basis weight and density for the sample using the average thickness is calculated.

Sample structure Examples 1 and 3 were also tested for tensile strength (N/inch) and elongation (%) according to TAPPI Methods T 494-OM-96 (1996); and Gurley Stiffness (mg) in the machine direction (CD) and cross-machine direction (MD) according to TAPPI Method T543 OM-94 (1994). In the test conducted for the articles of the invention, the CD testing measured delamination in the seal area, whereas the MD testing measured delamination at a location outside the seal area.

The results of the testing of sample articles A and B is shown below:

TABLE 3

Testing Results of Sample Absorbent Articles A and B

|  | Samples | |
| --- | --- | --- |
|  | A | B |
| Basis Weight (gsm) | 235 | 236 |
| Caliper (mm) | 1.09 | 1.04 |
| Particle Containment (mg) | 0.07 | 0.17 |
| Tensile Strength (N/inch) | 14.26 | 12.03 |
| Elongation (%) | 12.51 | 12.40 |
| CD Gurley Stiffness (mg) | 94.50 | 111.20 |
| MD Gurley stiffness (mg) | 152.90 | 141.80 |
| MD Delamination (avg. value) (N) | 0.646 | 0.848 |
| CD Delamination (peak value) (N) | 1.455 | 1.624 |

The exemplary absorbent cores were found to have total basis weights which were slightly in excess of the targeted basis weights. This differences were due to manufacturing conditions, and are commonly observed during the manufacture of fibrous structures.

Although the present invention has been described and illustrated with respect to a preferred embodiment and a preferred use thereof, it is not to be so limited since modifications and changes can be made therein which are within the full intended scope of the invention.

We claim:

1. A fibrous web comprising:
   (a) a lower stratum comprising thermoplastic fibers and matrix fibers which are cellulosic fibers or a blend of cellulosic fibers and synthetic fibers; and
   (b) an upper stratum comprising thermoplastic fibers and matrix fibers which are cellulosic fibers or a blend of cellulosic fibers and synthetic fibers;
   wherein a plurality of functional particle areas comprised of superabsorbent polymers are positioned between said upper stratum and said lower stratum so as to contact each of said upper and lower strata, each said functional particle areas being separated from other functional particle areas by a seal area comprising a seal formed between said upper and said lower strata.

2. The fibrous web of claim 1 wherein said seal area is substantially free of functional parties.

3. The fibrous web of claim 1 wherein said thermoplastic fibers are bicomponent fibers.

4. The fibrous web of claim 1 wherein said functional particle area comprises superabsorbent polymers.

5. The fibrous web of claim 4 wherein said functional particle area further comprises zeolites.

6. The fibrous web of claim 1, further comprising a binder on the entire surface of the fibrous web.

7. The fibrous web of claim 1 wherein said seal is formed by the application of pressure and/or heat.

8. The fibrous web of claim 1 wherein a binder is applied onto said seal area, said binder having a binder solids concentration of from 3 to 25% by weight, based on the total weight of the binder.

9. The fibrous web of claim 8 wherein said binder is applied onto said seal area is a latex binder.

10. The fibrous web of claim 1 having a powder spillage value of not more than 1.0 mg.

11. The fibrous web of claim 1 having a peak seal strength of greater than 0.6 N.

12. The fibrous web of claim 1 having a stiffness in the seal area of less than 150 mg.

13. The fibrous web of claim 1 having a stiffness in the non-seal area of less than 200mg.

14. An absorbent article comprising:
   (a) a lower stratum comprising thermoplastic fibers and cellulosic fibers or a blend of cellulosic fibers and synthetic fibers;
   (b) an upper stratum comprising thermoplastic fibers and cellulosic fibers or a blend of cellulosic fibers and synthetic fibers;
   (c) a functional particle area comprised of superabsorbent polymers positioned between said upper stratum and said lower stratum so as to contact each of said upper and lower strata; and
   (d) a seal area comprising a seal formed between said upper and said lower strata, said seal area being substantially free of functional particles.

15. The article of claim 14 said article comprising two said seal areas, wherein said seal areas are disposed on opposing edges of said article.

16. The article of claim 14 wherein said thermoplastic fibers are bicomponent fibers.

17. The article of claim 14 wherein said functional particle area further comprises zeolites.

18. The article of claim 14 wherein said seal is formed by the application of pressure and/or heat.

19. The article claim 14, said article further comprising a binder on the entire surface.

20. The article of claim 19 wherein a binder is applied onto said seal area, said binder having a binder solids concentration of from 3 to 25% by weight, based on 100% total weight of the binder.

21. The article of claim 20 wherein said binder applied onto said seal area is a latex binder.

22. The article of claim 14 having a powder spillage value of not more than 1.0 mg.

23. The article of claim 14 having a peak seal strength of greater than0.6 N.

24. The article of claim 19 wherein said binder is present in the amount of less than 5% by weight of said article.

25. The article of claim 14 having a stiffness in the seal area of less than 150 mg.

26. The article of claim having a stiffness in the non-seal area of less than 200 mg.

27. An absorbent article comprising:
(a) a fluid pervious topsheet;
(b) a second stratum in fluid contact with said fluid pervious top sheet, said stratum comprising thermoplastic fibers and cellulosic fibers or a blend of cellulosic fibers and synthetic fibers;
(c) an upper stratum comprising thermoplastic fibers and cellulosic fibers or a blend of cellulosic fibers and synthetic fibers;
(d) a functional particle area comprised of superabsorbent polymers positioned between said upper stratum and said lower stratum so as to contact each of said upper and lower strata;
(e) a seal area comprising a seal formed between said upper and said lower strata, said seal area being substantially free of functional particles; and
(f) a fluid impervious backsheet.

28. The absorbent article of claim 27 wherein said article is selected from the group of a diaper, an adult incontinence product and s feminine hygiene product.

* * * * *